United States Patent [19]

Gladfelter et al.

[11] Patent Number: 4,481,348

[45] Date of Patent: Nov. 6, 1984

[54] GLYCIDYL ETHER OF GEM-BIS(HYDROXYMETHYL) HYDROCARBONS

[75] Inventors: Elizabeth J. Gladfelter, St. Paul; Edgar R. Rogier, Minnetonka, both of Minn.

[73] Assignee: Henkel Corporation, Minneapolis, Minn.

[21] Appl. No.: 460,341

[22] Filed: Jan. 24, 1983

Related U.S. Application Data

[63] Continuation-in-part of Ser. No. 321,961, Nov. 16, 1981, abandoned.

[51] Int. Cl.$^3$ ............................................. G08G 59/22
[52] U.S. Cl. .................................... 528/103; 528/365; 528/374; 528/407; 549/555
[58] Field of Search ................ 549/555; 528/365, 374, 528/407, 103

[56] References Cited

U.S. PATENT DOCUMENTS

| | | | |
|---|---|---|---|
| 3,819,747 | 1/1974 | Bertram et al. | 528/216 X |
| 4,026,862 | 5/1977 | Smith et al. | 528/115 X |
| 4,117,361 | 9/1978 | Smith et al. | 528/103 X |
| 4,246,161 | 1/1981 | Smith et al. | 528/103 X |

*Primary Examiner*—Earl A. Nielsen
*Attorney, Agent, or Firm*—Ernest G. Szoke; Patrick J. Span

[57] ABSTRACT

The present invention describes short chain aliphatic compounds having a geminal configuration of glycidyl groups.

10 Claims, No Drawings

GLYCIDYL ETHER OF GEM-BIS(HYDROXYMETHYL) HYDROCARBONS

CROSS-REFERENCE TO RELATED APPLICATION

This application is a continuation-in-part of Ser. No. 321,961, filed on Nov. 16, 1981, now abandoned.

BACKGROUND OF THE INVENTION

1. Field of the Invention

This invention relates to the manufacture of low molecular weight polyglycidyl compounds which are useful as reactive diluents in epoxy formulations.

2. Description of the Art Practices

It is known in the art that glycidyl ethers may be cured by various means such as polyfunctional amines, or compounds which contain mixtures of amide and amine groups to form high molecular weight polymeric coatings such as paints. It is also known in the art that it is desirable to lower the viscosity of the high molecular weight polyepoxide compounds to facilitate mixing. Two classes of materials are used as diluents to lower the viscosity of the epoxide compounds used to form the coating. These two groups of materials are inert ingredients which have no reactive functionality and which are evaporated from the coating upon curing and diluents containing a monofunctional group in the compound. An example of the latter type of material is a monoepoxide such as Epoxide 7 or Epoxide 8 which are derived from straight chain fatty alcohol and available from Procter and Gamble.

It is, however, desirable to formulate a reactive diluent to take the place of inert diluents or only partially reactive diluents. The present invention accomplishes this by forming the glycidylate of a low molecular weight diol alcohol having a aliphatic backbone. Difunctional diluents are extremely useful in that they do not evaporate as do inert diluents which may be harmful to the environment, and are far more useful than monofunctional diluents which terminate polymer growth.

Recent advances in the production of polyglycidyl ethers include epoxy resins as described in U.S. patent application Ser. No. 081,950 filed Oct. 4, 1979 by Rogier now U.S. Pat. No. 4,339,389. The compounds taught in the '950 application describe the polyglycidyl ethers of geminal bis(hydroxymethyl) compounds containing an additional hydroxyl functionality which is glycidylated and a high molecular weight dihydric alcohol of a non-geminal configuration which is glycidylated. In U.S. patent application Ser. No. 257,674 filed on Apr. 27, 1981 by Rogier now U.S. Pat. No. 4,356,128 the production of polyhydroxymethyl compounds which contain a terminal nitrile group is described. Such compounds are disclosed as being useful as epoxy resin components in the commonly assigned co-pending application of Gladfelter et al Ser. No. 321,968, filed Nov. 16, 1981, now abandoned.

An important aspect of the present invention is the preparation of the hereinafter described compounds. The process for manufacturing the compounds is through the use of a phase transfer catalyst. Information on this subject is found in *Phase Transfer Catalysis Principles and Techniques* by Starks and Liotta, Academic Press, New York 1978. Additional background in the field of phase transfer catalysis is found in *Phase Transfer Catalysis in Organic Synthesis* by Weber and Gokel published by Springer-Verlag, New York 1977.

Additional information found in the patent literature concerning phase transfer catalysis include Japanese Pat. Nos. 141,708; 141,709 and 141,710 all published in 1979. Still further information on the subject of phase transfer catalysis is found in Russian Pat. No. 602-501 published in 1976.

Throughout the specifications and claims, percentages and ratios are by weight, pressures are gauge and temperatures are in degrees Celsius unless otherwise noted. To the extent that each of, the foregoing references are applicable to the present invention they are herein incorporated by reference.

SUMMARY OF THE INVENTION

The present invention describes the diglycidyl ether of the structure

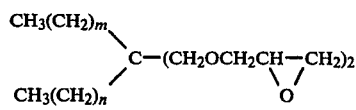

wherein m has a value of from 1 to 4 and n has a value of from 1 to 5.

DETAILED DESCRIPTION OF THE INVENTION

The invention as previously noted concerns polyglycidyl ethers of low molecular weight geminal alcohols having an aliphatic backbone. These compounds have the general formula as shown in the Summary of the Invention. Such compounds may be obtained from olefins which have been subjected to hydroformylation followed by a Crossed-Cannizaro reaction. The reader is referred to the work of Rogier previously herein incorporated by reference for a detailed description on how such compounds may be obtained. Such compounds will be obtained in mixtures as the bis(hydroxymethyl) group obtained from such a reaction will add to either of the carbons which previously contained the unsaturation in the molecule. However, such is not particularly important to the purposes of the present invention as essentially equal mixtures displaced by one carbon atom of the geminal alcohol are obtained.

In particular, it is valuable to select a starting material which will give values where the sum of m plus n as shown in the Summary of the Invention are from 2 to 7, preferably where m has values of from 2 to 3 or from 1 to 3. Additional valuable variations of the present invention are where n equals 2 to 4 and sum of m plus n is from 3 to 6. A particularly valuable embodiment of the present invention is found where m is 3 and n is 1 corresponding to 2-ethyl-2-butyl-1,3-propane diol. While the foregoing compound is a solid, it becomes a liquid when converted to the glycidyl ether. The starting compound 2-ethyl-2-butyl-1,3-propane diol is obtained from BASF or Pfaltz & Bauer, Inc. BASF is located in Wyandotte, Mich. while the latter firm is located in Stamford, Conn.

Having described the starting materials, the second step is to discuss for obtaining the polyglycidyl ether. Any convenient epihalohydrin may be employed to react to the hydroxymethyl groups of starting geminal compound. Most conveniently, the epihalohydrin is epichlorohydrin used in excess amounts. The reaction may be run using a solvent such as tetrahydrofuran or toluene.

The preferred method for conducting the reaction is to carry out the reaction in a two phase system one of which is an aqueous alkaline phase. Conveniently, sodium hydroxide is used in an aqueous phase at from about 20 to about 60 percent by weight. The geminal polyhydric compound, the later described phase transfer catalyst and the epihalohydrin are combined and added to the aqueous base.

The reaction process is allowed to be maintained at from about 10 to about 80 degrees C., preferably 20 to 50 degrees C. until the reaction is complete.

The particular phase transfer catalysts which are utilized in the present invention include tetrahexylammonium chloride, benzyl triethylammonium chloride, and tetrabutylammonium chloride.

Upon completion of the reaction, the product is diluted with water and the organic layer washed and dried conveniently using sodium sulfate.

After the compound has been isolated it may be used as the sole epoxy reactant or as a reactive diluent for an epoxy compound such as Bisphenol A or a Bakelite. The epoxy of the present invention is conveniently combined with an acid polyanhydride, polyacids, mercaptans or polyamine to form a cured epoxy resin.

Among the advantages of the difunctional diluent of the present invention are that the cured epoxy compounds exhibit high flexibility and higher heat distortion resistance. The overall viscosity of an epoxy resin mixture containing the reactive diluent is lower than those employing known reactive diluents. The halogen content of the compounds is quite low compared to other epoxy compounds. There is also the additional advantage that the compounds are distillable to a product substantially free of halogen. Thus products of less than 0.5% halogen are obtainable.

The difunctional diluent is conveniently employed in an epoxy resin formulation at levels of about 5% to about 50% preferably 10% to 40% by weight of the total glycidyl material present.

The following are examples of the present invention.

EXAMPLE I

The diglycidyl ether of 2-ethyl-2-butyl-1,3-propane diol is prepared as follows. A 50 percent aqueous solution of sodium hydroxide comprising 42.7 grams is placed in a reaction vessel containing a condenser, dropping funnel and an inert gas inlet. The diol, at 10.7 grams is mixed with the phase transfer catalyst, tetrabutyl ammonium chloride, at 0.73 grams and epichlorohydrin at 24.7 grams. This second mixture is then slowly added to the aqueous base over a period of 1 hour with the temperature in the vessel maintained at 40 degrees C. with stirring. After a period of approximately 5 hours the reaction is substantially complete and the reaction mixture is diluted with 100 grams of water. The organic layer is then water washed, dried over sodium sulfate and analyzed. The reaction mixture shows that the diglycidyl ether is present at 11.3 percent on an oxirane content basis.

EXAMPLE II

The diglycidyl ether of 2-ethyl-2-butyl-1,3-propane diol is prepared by placing a 50 percent aqueous sodium hydroxide solution at 480 grams in a reaction vessel such as that described in Example I. A mixture of 346.9 grams of epichlorohydrin, 120 grams of tetrahydrofuran at 120 grams (solvent), 8.3 grams of tetrabutylammonium chloride as the phase transfer catalyst and the diol at 120 grams are combined. This mixture is added to the aqueous caustic with stirring while maintaining the reaction temperature at 40 degrees C. for a period of 5 hours.

At the end of this period the mixture is allowed to phase separate. The organic layer is washed several times with water and the pH adjusted to 8 using dry ice. Traces of solvent and water are removed under vacuum. The product mixture is filtered under pressure through a 0.1 micron pad. The oxirane content obtained corresponds to an average of 9.3%. The total chlorine content in the molecule is 0.94 percent.

EXAMPLE III

Epoxy coatings are prepared and tested according to the information given in Tables 1 and II following:

TABLE I

| GLYCIDYL ETHER TESTED | DILUENT/ EPON 828 | CHEMICAL RESISTANCE PROPERTIES* | | | | | | | |
|---|---|---|---|---|---|---|---|---|---|
| | | % WEIGHT GAIN OR LOSS AFTER 21 DAYS IMMERSION IN: | | | | | | | |
| | | 10% HCl | 10% NaOH | 10% $H_2SO_4$ | 10% $CH_3COOH$ | Distilled Water | Xylene | Mineral Spirits | MEK |
| Epon 828** | 0/100 | 1.25 | 0.59 | 1.05 | 6.52 | 0.80 | 0.10 | 0.09 | 15.87 |
| Product of Example II | 23/77 | 2.15 | 1.00 | 3.72 | 9.46 | 1.02 | 0.40 | 0.57 | 4.87 |
| DER 736*** | 30/77 | 4.22 | 1.07 | 6.22 | 15.21 | 1.48 | 0.29 | 0.40 | 2.90 |

*All epoxy resin systems were cured with triethylenetetramine at a 1 to 1 equivalence ratio of epoxide to amine hydrogen. Cure cycle was a 16 hour gel at ambient temperatures followed by a 24 hour post cure at 60° C.
**Aromatic epoxy from Shell.
***Commercial reactive diluent from Dow which is a polyglycol diepoxide.

TABLE II

| GLYCIDYL ETHER TESTED | DEN 438 WEIGHT RATIO DILUENT/EPON 828 | RESIN VISCOSITY[1] | PHYSCIAL PROPERTY TESTING* | | | | | |
|---|---|---|---|---|---|---|---|---|
| | | | HEAT DISTORTION | | TENSILE STRENGTH[2] | | TENSILE ELONG | |
| | | | 60° C. | 110° C. | 60° C. | 110° C. | 60° C. | 110° C. |
| Epon 828 | 0/100/0 | 11,000 – 14,000 | 91° C. | 108° C. | 11,103 | 8,959 | 8.25% | 7.00% |
| Product from Example I | 23/77/0 | 1,000 | 83° C. | 84° C. | 10,755 | 9,668 | 10.58% | 9.79% |
| Product from Example II | 30/70/0 | 500 | — | — | — | — | — | — |

TABLE II-continued

| | | PHYSCIAL PROPERTY TESTING* | | | | | | |
|---|---|---|---|---|---|---|---|---|
| GLYCIDYL ETHER TESTED | DEN 438 WEIGHT RATIO DILUENT/EPON 828 | RESIN VISCOSITY[1] | HEAT DISTORTION | | TENSILE STRENGTH[2] | | TENSILE ELONG | |
| | | | 60° C. | 110° C. | 60° C. | 110° C. | 60° C. | 110° C. |
| DER 736 | 30/70/0 | 900 | 65° C. | 77° C. | 9,978 | 9,419 | 11.00% | 10.70% |
| Product from Example I | 30/0/70 | | | 101° C. | | | | |
| DER 736 | 30/0/70 | | | 88° C. | | | | |

All epoxy resin systems were cured with triethylenetetramine at a 1 to 1 equivalence ratio of epoxide to amine hydrogen. Cure cycle was at 16 hour gel time at ambient followed by a 24 hr. post cure at 60° C. or a 2 hour post cure at 110° C.
[1]Viscosity measured in cp.
[2]Tensile strength measured in psi.
The viscosity of resins using the diglycidyl diluent of the invention are quite low. The heat distortion properties of the products formulated with the diglycidyl diluent are better than the DER 736 as is the tensile strength.

What is claimed is:

1. A diglycidyl ether of the formula

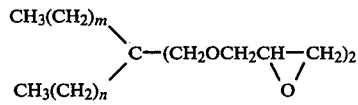

wherein m has a value of from 1 to 4 and n has a value of from 1 to 5.

2. The composition of claim 1 which is substantially free of halogen.

3. The composition of claim 1 wherein the sum of m plus n is from 2 to 7.

4. The composition of claim 1 wherein m is 2 to 3.

5. The composition of claim 1 wherein n is from 2 to 4.

6. The composition of claim 1 wherein the sum of m plus n is from 3 to 6.

7. The composition of claim 1 wherein m is 2 to 3 and n is from 1 to 3.

8. The composition of claim 1 wherein m is 1 and n is 3.

9. The composition of claim 1 cured with a member selected from the group consisting of polyamines, polyacids, polyanhydrides and mercaptans.

10. The composition of claim 1 wherein the diglycidyl ether is present at from about 5% to 50% of the total glycidyl content of an epoxy resin composition.

* * * * *

UNITED STATES PATENT AND TRADEMARK OFFICE
CERTIFICATE OF CORRECTION

PATENT NO. : 4,481,348
DATED : Nov. 6, 1984
INVENTOR(S) : Elizabeth J. Gladfelter and Edgar R. Rogier It is certified that error appears in the above-identified patent and that said Letters Patent are hereby corrected as shown below:

In Claim 4, at column 6, line 16, the phase "2 to 3" should read:

-- 2 or 3 --.

In Claim 7, at column 6, line 21, the phrase "2 to 3" should read:

-- 2 or 3 --.

Signed and Sealed this

Thirtieth Day of April 1985

[SEAL]

Attest:

DONALD J. QUIGG

Attesting Officer          Acting Commissioner of Patents and Trademarks